United States Patent [19]

Adams

[11] Patent Number: 4,693,253
[45] Date of Patent: Sep. 15, 1987

[54] AUTOMATIC IMPLANTABLE DEFIBRILLATOR AND PACER
[75] Inventor: Theodore Adams, Edina, Minn.
[73] Assignee: Medtronic, Inc., Minneapolis, Minn.
[21] Appl. No.: 246,528
[22] Filed: Mar. 23, 1981
[51] Int. Cl.$^4$ ............................................. A61N 1/36
[52] U.S. Cl. ......................... 128/419 D; 128/419 PS
[58] Field of Search ....................... 128/419 D, 419 PS
[56] References Cited
U.S. PATENT DOCUMENTS 3,614,955 10/1971 Mirowski ........................ 128/419 D
3,716,059  2/1973 Welborn et al. ............... 128/419 D
3,747,605  7/1973 Cook .............................. 128/419 D
4,015,609  4/1977 Mensink et al. .............. 128/419 PS Primary Examiner—William E. Kamm
Attorney, Agent, or Firm—Robert C. Beck; Joseph F. Breimayer; John L. Rooney

[57] ABSTRACT

A defibrillator/pacer having separate energy storage circuits for pacing and defibrillating. The pacing energy storage is charged from residual energy from the defibrillator source to permit high energy pacing after defibrillation. In operation, energy is transferred from the defibrillation energy storage source to the pacing energy storage source which is utilized to provide energy for pacing the heart after defibrillation.

4 Claims, 4 Drawing Figures

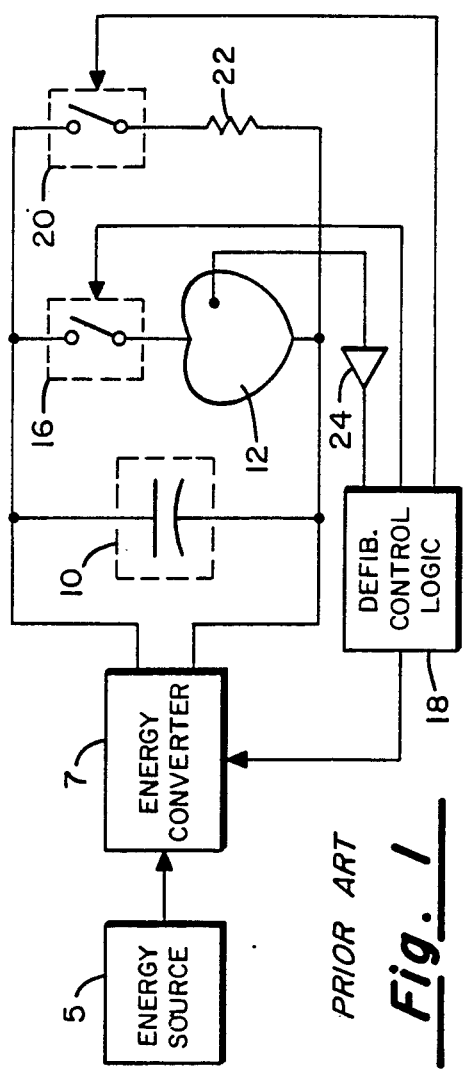
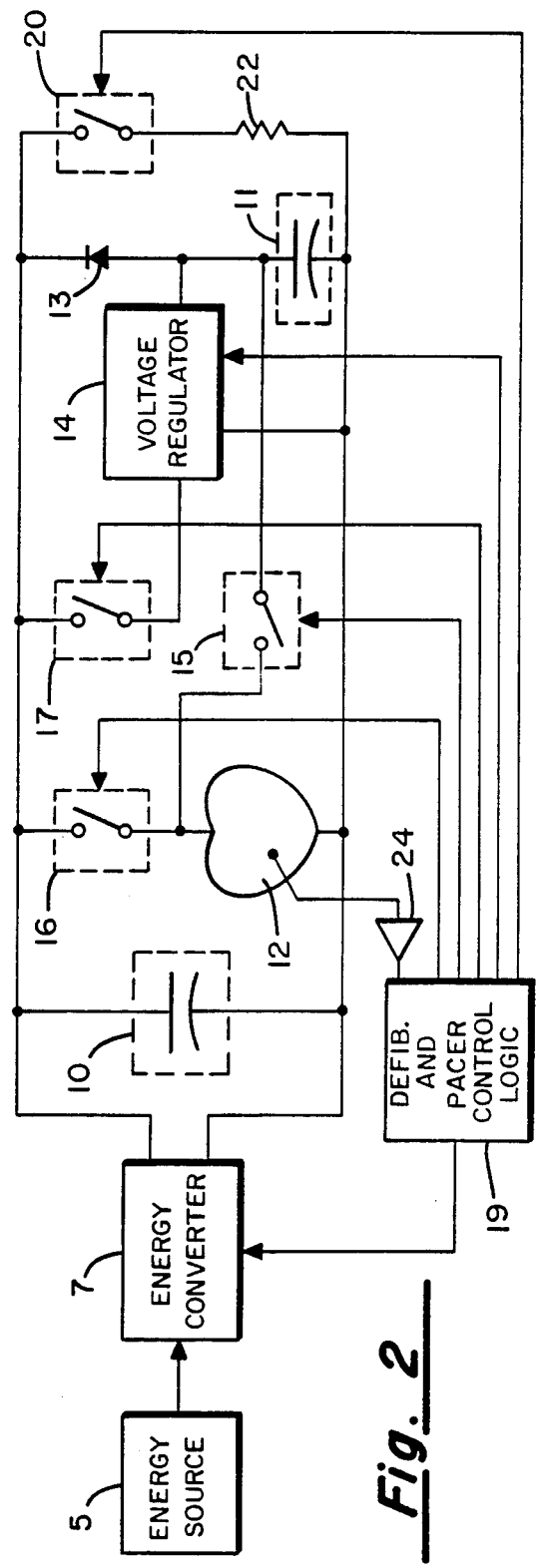

AUTOMATIC IMPLANTABLE DEFIBRILLATOR AND PACER

BACKGROUND OF THE INVENTION

1. Field of the Invention.

This invention relates generally to automatic implantable defibrillators and, more particularly, to an automatic implantable defibrillator which includes a pacing, pulse generator for delivering high energy cardiac stimulating pulses to the heart after defibrillation.

2. Description of the Prior Art.

Ventricular fibrillation is a lethal cardiac arrhythmia which is characterized by disorganized electrical activity in the heart coupled with low cardiac output. The traditional treatment for ventricular fribrillation has been the delivery of a cardioverting shock to the heart to bring about the simultaneous depolarization of all of the cardiac tissue. Typically, this cardioverting shock is delivered through external paddles applied to the chest of the patient as shown in U.S. Pat. No. 3,716,059 to Welborn, et al., which discloses an external defibrillator unit coupled with a pacemaker.

An implantable form of the defibrillator is known from U.S. Pat. Nos. 3,614,954 and 3,614,955 to Mirowski, et al. Each of these devices is provided with means for detecting ventricular fibrillation and for delivering a relatively high energy cardioverting pulse (40 joules) to the heart.

Research has shown that the most effective waveform for this defibrillating or cardioverting pulse is a trapezoidal waveform. An example of a defibrillator output circuit which will deliver a trapezoidal waveshape into the heart is known from U.S. Pat. No. 3,706,313 to Milani, et al. This patent teaches the use of a current source for charging a capacitor to a high energy level which is discharged through the heart through a silicon-controlled rectifier, which is operated as a switch. A second silicon-controlled rectifier then dissipates the remaining energy on the energy storage capacitor through a resistive load, not associated with the patient's heart. This circuit provides an alternate discharge path where the energy stored in the defibrillating capacitor is discharged to circuit ground.

SUMMARY OF THE INVENTION

In contrast to the prior art, the apparatus of the present invention does not dissipate the residual charge on a defibrillating capacitor. The pacer of the present invention utilizes the residual energy available from the cardioverting energy source to provide high energy pacing pulses to the heart after cardioversion.

BRIEF DESCRIPTION OF THE DRAWINGS

FIG. 1 is a functional block diagram of a prior art automatic implantable defibrillator;

FIG. 2 is a functional block diagram of the automatic implantable defibrillator and pacer of the present invention;

DETAILED DESCRIPTION OF THE PREFERRED EMBODIMENT

Figure 3:
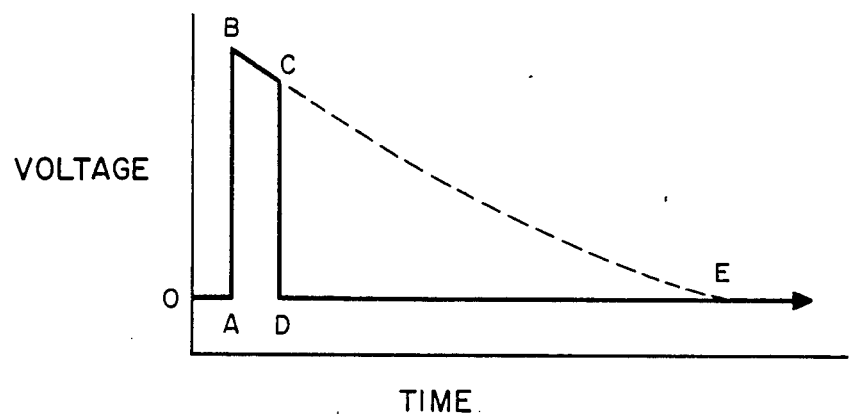
FIG. 3 is a waveform diagram of a prior art defibrillator discharge.

The prior art device shown in FIG. 1 includes cardioverting circuitry coupled to the patient's heart 12. This prior art device includes a primary energy source 5 coupled to energy converter 7 for charging the energy storage capacitor 10 to a high voltage level.

Switches 16 and 20 discharge the energy stored on the energy storage capacitor 10 in response to control signals generated by defibrillator control logic 18. During cardioversion, the heart is connected to the energy source by the closure of switch 16. After the energy source has been discharged to a second preset voltage level, switch 16 is opened and switch 20 is closed to dissipate the remaining energy stored in capacitor 10.

During normal operation, a sense amplifier 24 monitors cardiac activity from the heart; and if ventricular fibrillation is detected, the logic 18 will activate the DC/DC energy converter 7 which charges up the energy storage means 10 from a primary battery source 5. After an appropriate amount of energy is stored within the energy storage means 10, the logic 18 activates switch 16 discharging the energy source from a high voltage level to a lower voltage level. This is shown diagrammatically on FIG. 3 where segment AB corresponds to the charging of the capacitor. Segment BCD corresponds to the defibrillating discharge. Upon detection of fibrillation, the energy storage means is charged from a voltage A up to a voltage B which may typically be 1,000 volts. After switch 16 is activated, the energy storage means will discharge through the heart to a second voltage level indicated by point C on the diagram corresponding to approximately 500 volts over a time period of approximately 10 milliseconds as indicated by the width of the pulse. The energy storage means is then isolated from the heart which corresponds to segment CD in FIG. 3.

In this prior art device after the voltage level C is reached, the residual energy of the capacitor is dissipated in a resistive load 22 corresponding to the discharge from C to E.

The invention, as shown in FIG. 2, may be contrasted to the prior art in that after the initial defibrillating waveform is delivered to the heart, the residual energy is retained and used to provide energy for pacing pulses.

In operation, the sensing circuitry 24 monitors the cardiac activity from the heart 12 and produces a signal delivered to defibrillator and pacer logic 19 which is used for the detection of fribrillation. Logic 19 responds by initiating the charging of energy storage means 10 by energy converter 7. After an appropriate amount of energy is stored in energy storage means 10, a signal from logic 19 to switch 16 connects the heart 12 to the energy storage device 10 and results in a discharge of some energy stored in energy storage device 10. After an appropriate duration, the switch 16 is opened permitting the residual energy to be retained by energy storage device 10. If the cardiac tissue does not return to a normal sinus rhythm after a time period indicated by the escape interval timing ET on the diagram of FIG. 4, then some of the residual energy stored within energy storage means 10 will be delivered to the heart in the form of a pacing stimulus. In this fashion, the automatic implantable defibrillator and pacer of the present invention permits the high energy stimulation of the cardiac tissue if the cardioverting pulse delivered to the heart has prevented the prompt reestablishment of normal sinus rhythm. Additional pacing stimuli may be produced in response to an extended interruption of the cardiac cycle.

In the simplest form of the invention, energy may be taken directly from energy storage capacitor 10 and coupled through the heart for pacing purposes by means of switch 16. However, it may be more desirable to lower the voltage extant on the energy storage capacitor 10 to a lower level. A system to provide this feature is shown in FIG. 2 wherein energy from the energy storage capacitor 10 may be coupled through a voltage regulator 22 by closure of switch 17. This will charge pacing capacitor 11 to a voltage level less than that available at energy storage capacitor 10. Energy from this pacing storage capacitor 11 may then be coupled to the heart through the operation of switch 15 in response to defibrillator and pacing control logic 19.

After normal sinus rhythm is restored and there is no further need for pacing or defibrillating energy, it may be desirable to discharge both of the energy storage capacitors 10 and 11. This may be accomplished by closure of switch 20 which discharges the energy on the defibrillating energy storage capacitor 10 as well as the pacing capacitor 11.

Figure 4:
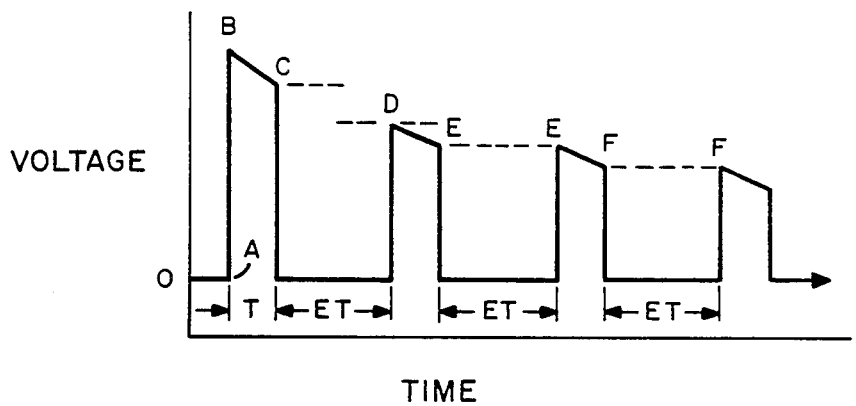
FIG. 4 is a waveform diagram illustrating the defribillating and pacing output of the present invention.

The operating modality of this form of the invention is shown on FIG. 4 wherein the defibrillating capacitor is charged from a voltage level A to a voltage level B. The heart is defibrillated by the discharge of energy from voltage B to voltage C through the cardiac tissue. Energy is subsequently transferred by means of the voltage regulator 22 to the pacing storage capacitor at a voltage D as shown in the waveform of FIG. 4. Subsequent pacing pulses corresponding to the energy discharged from point D to point E and point E to point F may be delivered periodically to the heart to initiate cardiac depolarizations.

The switches of the present invention shown as 15, 16, 17 and 20 in the figures must exhibit a high impedance in the OFF state and a low impedance in the ON state. These switches must be operable by low level logic signals produced by logic means 18. It is presently contemplated that metal oxide semiconductor power transistors will be suitable for this component.

It should be apparent from the foregoing that modifications may be made to the invention without departing from its spirit and scope.

I claim:

1. An implantable defibrillator and pacer for cardioverting and pacing a patient's heart comprising:

a lead system for coupling the patient's heart to said defibrillator and pacer and for delivering cardioverting and pacing energy to the heart;

a sense amplifier for coupling to the heart for detecting the depolarization of cardiac tissue;

first energy storage means for storing both said cardioverting energy and pacing energy;

a primary energy source means for supplying energy to said first energy storage means;

an energy converter coupled to said primary energy source and said first energy storage means for supplying energy to said first energy storage means at a voltage higher than the voltage of said primary energy means;

second energy storage means for storing said pacing energy;

first switch means coupled to said first energy storage means for delivering said cardioverting energy to said lead system in response to a first control signal;

a voltage regulator coupled to said first storage means for charging said second storage means in response to a second control signal;

a second switch means for coupling said second energy storage means to said lead system in response to a third control signal;

defibrillation and pacer control logic coupled to said sense amplifier for detecting fibrillation, and for producing said first control signal in response to the detection of fibrillation;

said defibrillation and control logic for producing said second control signal after the delivery of said cardioverting energy; and, said defibrillation pacer control logic defining an escape time interval and for producing said third control signal if no cardiac depolarization is detected by said sense amplifier during said escape time interval.

2. The implantable defibrillator and pacer of claim 1 further including a switch, wherein said voltage regulator is coupled to said first storage means through said switch which is actuated by a fourth control signal developed by said defibrillation and pacer control logic after cardioverting energy is supplied to the lead system.

3. The implantable defibrillator and pacer of claim 1 or 2 further including a resistor means wherein, said switch means are coupled in series to said resistor means for discharging said first and second energy storage means in response to a fifth control signal developed by said defibrillation and pacer control logic after fibrillation has been cardioverted.

4. The device of claim 1 or claim 2 wherein the operation of said energy converter is initiated through a first control signal developed by said defibrillation and pacer control logic in response to the detection of fibrillation.

* * * * *

UNITED STATES PATENT AND TRADEMARK OFFICE
CERTIFICATE OF CORRECTION

PATENT NO. : 4,693,253
DATED : September 15, 1987
INVENTOR(S) : Theodore Adams

It is certified that error appears in the above-identified patent and that said Letters Patent are hereby corrected as shown below:

Column 3,
  Line 22, "modality" should be --mode--;

Line 23, after "shown", add --in an exaggerated scale for clarity on Fig. 4. In the figure, the--;

Line 23, after the second occurrence of the word "the", please delete "on FIG. 4 wherein the";

Line 32, after "periodically", add --at appropriate escape interval times labeled ET in the figure--;

Line 32, after "figure", please delete "to the heart";

Line 35, please delete "must", and insert --should--;

Line 37, please delete "must", and insert --should--.

Signed and Sealed this

Seventeenth Day of May, 1988

Attest:

DONALD J. QUIGG

*Attesting Officer*  *Commissioner of Patents and Trademarks*